(12) United States Patent
Taylor

(10) Patent No.: US 7,066,939 B2
(45) Date of Patent: Jun. 27, 2006

(54) CONNECTION ASSEMBLY FOR SPINAL IMPLANT SYSTEMS

(75) Inventor: Harold Sparr Taylor, Memphis, TN (US)

(73) Assignee: SDGI Holdings, Inc., Wilmington, DE (US)

( * ) Notice: Subject to any disclaimer, the term of this patent is extended or adjusted under 35 U.S.C. 154(b) by 632 days.

(21) Appl. No.: 10/426,740

(22) Filed: Apr. 30, 2003

(65) Prior Publication Data

US 2003/0191473 A1    Oct. 9, 2003

Related U.S. Application Data

(62) Division of application No. 09/883,580, filed on Jun. 18, 2001, now Pat. No. 6,579,292.

(51) Int. Cl.
*A61B 17/58* (2006.01)

(52) U.S. Cl. ....................................................... 606/61

(58) Field of Classification Search .................. 606/53, 606/54, 60, 61, 69, 70, 71, 72, 73; 403/390, 403/396, 400, 346
See application file for complete search history.

(56) References Cited

U.S. PATENT DOCUMENTS

| | | | | |
|---|---|---|---|---|
| 4,987,892 A | * | 1/1991 | Krag et al. | 606/61 |
| 5,047,029 A | * | 9/1991 | Aebi et al. | 606/61 |
| 5,053,034 A | | 10/1991 | Olerud | |
| 5,411,523 A | | 5/1995 | Goble | |
| 5,505,731 A | * | 4/1996 | Tornier | 606/61 |
| 5,624,440 A | * | 4/1997 | Huebner | 606/59 |
| 5,643,263 A | | 7/1997 | Simonson | |
| 5,645,599 A | * | 7/1997 | Samani | 623/17.16 |
| 5,681,135 A | | 10/1997 | Simonson | |
| 5,885,285 A | | 3/1999 | Simonson | |
| 5,947,967 A | | 9/1999 | Barker | |
| 6,004,323 A | | 12/1999 | Weinstein | |
| 6,056,753 A | | 5/2000 | Jackson | |
| 6,183,473 B1 | | 2/2001 | Ashman | |
| 6,234,705 B1 | | 5/2001 | Troxell | |
| 6,248,107 B1 | * | 6/2001 | Foley et al. | 606/61 |
| 6,520,962 B1 | | 2/2003 | Taylor et al. | |
| 2002/0013585 A1 | | 1/2002 | Gournay et al. | |

FOREIGN PATENT DOCUMENTS

GB        1517269        7/1978

\* cited by examiner

*Primary Examiner*—Eduardo C Robert
*Assistant Examiner*—James L Swiger
(74) *Attorney, Agent, or Firm*—Woodard, Emhardt, Moriarty, McNett & Henry LLP

(57) ABSTRACT

Disclosed is a novel connection assembly for a spinal implant system having:
  a novel interface element having an internal stop that limits rotation of the spinal implant rod and associated members with regard to the spinal implant bolt and associated members allowing the implant system to initially assume a position that approximates its final adjusted position and allows the assembly's size to be reduced without sacrificing its mechanical strength;
  a compressible member located between the interface elements that ensures free rotation of the spinal implant rod and its associated members in relation to the spinal implant bolt and its associated members until a proper position has been obtained and allows an initially secured system to be repositioned without additionally separating the interface element's locking structures;
  and components provisionally secured to prevent disengagement during transportation and handling that can be engaged during installation utilizing minimal force with common hand tools.

23 Claims, 4 Drawing Sheets

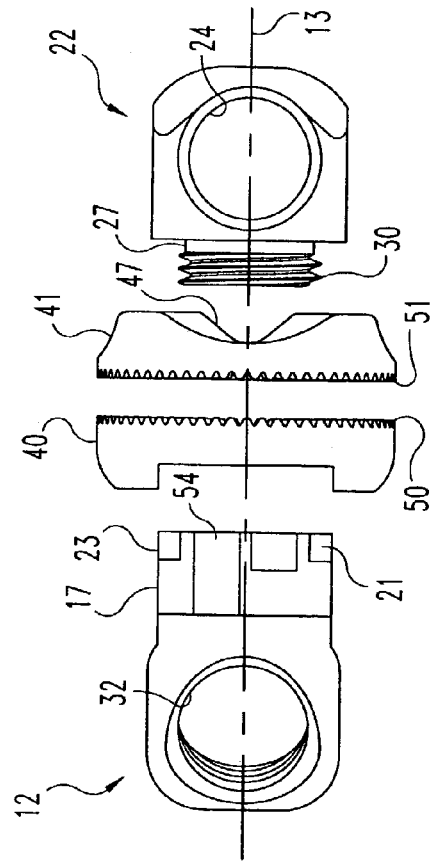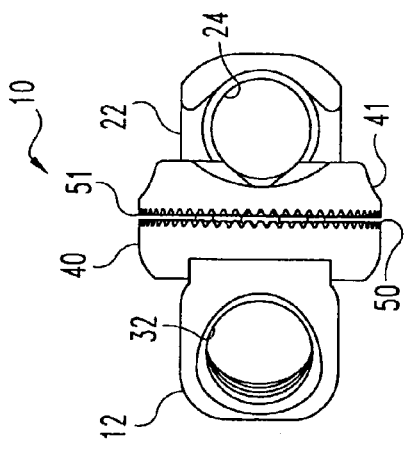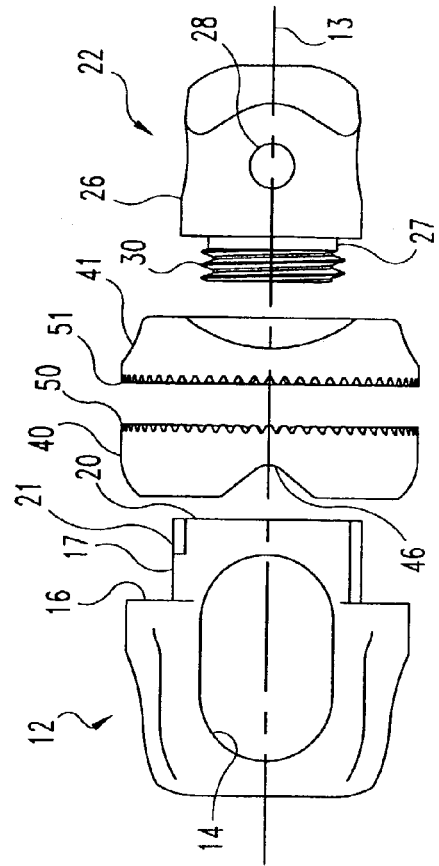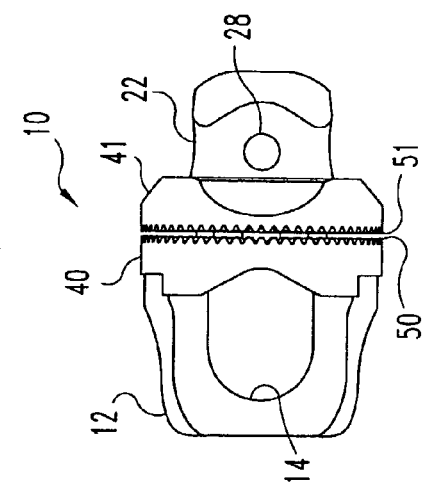

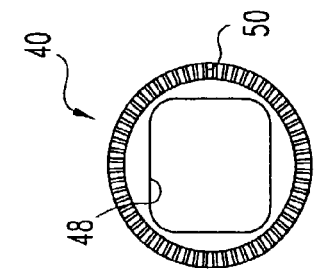
*Fig. 5*
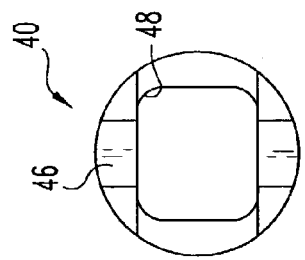
*Fig. 6*
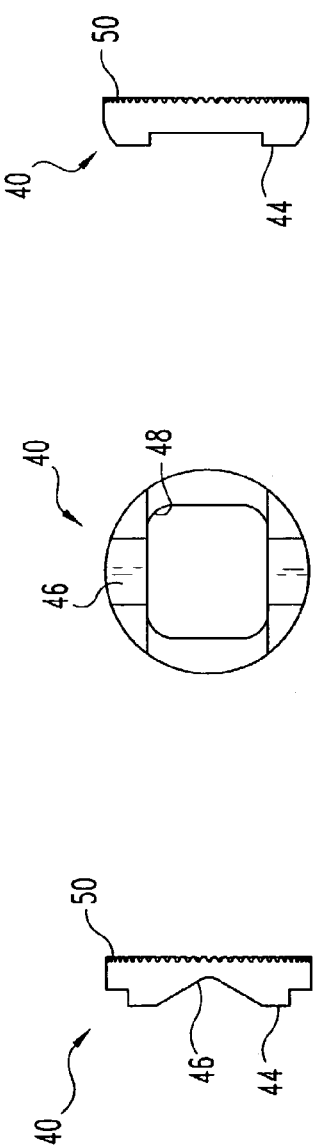
*Fig. 7*
*Fig. 8*
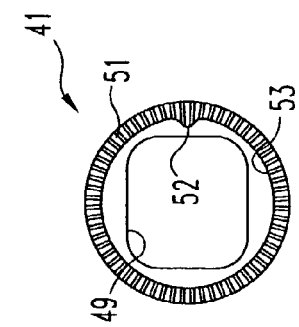
*Fig. 9*
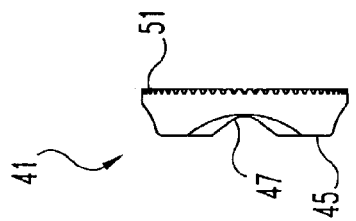
*Fig. 10*
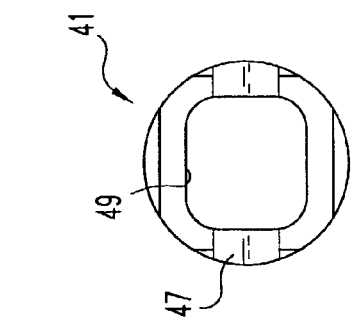
*Fig. 11*
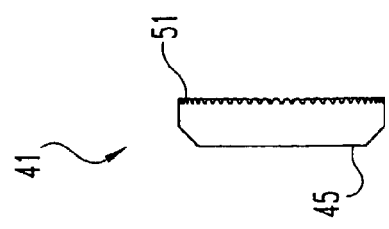
*Fig. 12*

CONNECTION ASSEMBLY FOR SPINAL IMPLANT SYSTEMS

REFERENCE TO RELATED APPLICATIONS

This application is a divisional and claims priority upon U.S. patent application Ser. No. 09/883,580 filed Jun. 18, 2001, now U.S. Pat. No. 6,579,292, which is hereby incorporated by reference in its entirety.

BACKGROUND OF THE INVENTION

Spinal implant systems provide a rod for supporting and positioning the spine in response to the specific problem being corrected by the implant and the patient's particular anatomy. The systems comprises a support rod, bolts secured to vertebrae and a connector that securely engages the support rod to the connecting bolts and allows the system to assume positions where the rod is maintained at various angles in response to the problem being corrected and the patient's particular anatomy. Although implant systems currently available satisfy these basic needs, further refinements are needed in the design of the connection assemblies utilized. Connection assemblies are needed that: minimize the assembly preparation prior to installation; can quickly assume and maintain an approximate position in the initial phase of installation, then be quickly and easily locked into position to complete the installation; have the ability to be repositioned with minimal effort after initially secured; and require minimal space in the patient's spinal region for installation.

SUMMARY OF THE INVENTION

It is one object of the present invention to provide a connection assembly for a spinal implant system having components that limit the rotation of a spinal implant rod in respect to a corresponding spinal implant bolt, cause the initially implanted system to assume and maintain a position that approximates its final position and allow the system to be easily secured when the appropriate position has been attained. The structure limiting rotation is an interface element having an internal stop within an internal circumference or internal periphery, the internal stop positioned to contact other internal structures such as two edges of a seat maintaining a second interface element. The nature of the internal stop and its placement allow the connection assembly's size to be reduced without sacrificing the assembly's performance.

In one aspect of the present invention, a connection assembly for connecting a spinal implant rod to a spinal implant bolt is provided, the assembly comprising: a rod connecting member having an opening for receiving a portion of the rod, and a first interface element on the rod connecting member; a bolt connecting member attached to the rod connecting member, the bolt connecting member having an opening for receiving a portion of the bolt, and a second interface element on the bolt connecting member; the first interface element being fixed against rotation relative to the rod connecting member and the second interface element having a disengaged condition wherein the rod connecting member and bolt connecting member are rotatable within a limited range relative to one another, the limited range defined by an internal stop element positioned within an inner periphery of one of the interface elements; and the first interface element and the second interface element having an engaged condition wherein the rod connecting member and bolt connecting member are fixed against rotation relative to one another. Connection assemblies according to this embodiment of the present invention have structural features that provide for reduction in the assembly's size, that allow the assembly to approximate a final installed position early in the installation process while the assembly's interface elements are in a disengaged condition and allow the assembly to be quickly and easily secured to maintain an appropriate position once the elements assume an engaged condition.

It is a further object of the present invention to provide connection assembly for connecting a spinal implant rod to a spinal implant bolt wherein the assembly can be initially secured and subsequently re-positioned and re-secured with minimal effort as needed. In one aspect of the present invention, a connection assembly for connecting a spinal implant rod to a spinal implant bolt is provided, the assembly comprising: a rod connecting member having an opening for receiving a portion of the rod; a first interface element on the rod connecting member; a bolt connecting member having an opening for receiving a portion of the bolt; a second interface element on the bolt connecting member, the first interface element being fixed against rotation relative to the rod connecting member and the second interface element being fixed against rotation relative to the bolt connecting member, the rod connecting and the bolt connecting members rotatably attached about a connection axis, one member opposing the other; interlocking structures on opposing surfaces of the interface elements, such that when the elements are engaged with one another, the interlocking structures prevent rotational movement of the interface elements relative to one another; and a compressible member positioned between the interface elements, the compressible member in its uncompressed state preventing the interlocking structures from engaging. Connection assemblies according to this embodiment of the present invention have a compressible member positioned between the interface elements that in its uncompressed state prevents engagement of the interlocking structures, in its compressed state allows the interlocking structures to become engaged to prevent rotation of one interface element relative to another interface element, and upon returning to its uncompressed state separates the interlocking structures associated with the interface elements allowing the interface elements to once again rotate for repositioning.

It is a further object of the present invention to provide a medical assembly comprising first and second assembled components, wherein the components are provisionally secured in their assembled configuration by a biocompatible material, and wherein the biocompatible material is disruptable during installation of the medical assembly. Additionally, the biocompatible material may also be capable of being resorbed by the body. Preferred embodiments of the present invention maintain their configuration during normal shipping and handling and during installation allow disruption of the provisionally secured component utilizing hand tools and forces reasonable within a surgical environment.

It is a still further object of the present invention to provide for an interface element having structural features that cooperate with other structural features of a connection system to restrict rotation of the interface element and any associated component about a central axis. In one aspect of the present invention, an interface element for use in a connection assembly is provided, the interface element comprising: a structure having at least one face; a central opening for receiving a structural element of a rod connecting member or a bolt connecting member and resist rotation relative thereto; and at least one internal stop element located about an inner periphery of the interface element. The utilization of interface elements of the present invention in connection assemblies allows the size of the assembly to be reduced without sacrificing the assembly's mechanical strength. Connection assemblies utilizing the novel interface element take up less space within a patient while still facilitating installation by providing restricted rotation of the rod connecting and bolt connecting members. As a result, a spinal implant system utilizing the assembly can be smaller without sacrificing performance.

It is a still further object of the present invention to provide a method to provisionally secure a component of a medical device therein, but allow the secured component to be subsequently engaged or removed. In one aspect of the present invention, a method is provided for provisionally securing components of a medical device, the method comprising: providing at least two components of a medical assembly to be provisionally secured, the components having surfaces suitable for engagement; applying a biocompatible material to at least one of the surfaces; contacting the surfaces to be secured; and maintaining contact of the surfaces until the components have been provisionally secured. Components of medical devices secured by this method remain in place after manufacture and during shipment and subsequent handling and can be engaged as necessary with minimal effort utilizing common hand tools and forces appropriate to a surgical environment to effect installation of the device in the usual manner.

BRIEF DESCRIPTION OF THE DRAWINGS

FIG. 1 is a plan view of a connection assembly for a spinal implant device according to the illustrated embodiment of this invention.

FIG. 2 is a plan view in exploded form.

FIG. 3 is a front elevation view.

FIG. 4 is a front elevation view in exploded form.

FIG. 5 is a front elevation of a first interface element according to the illustrated embodiment of this invention.

FIG. 6 is a side elevation.

FIG. 7 is a plan view.

FIG. 8 is an opposite side elevation.

FIG. 9 is a front elevation of a second interface element according to the illustrated embodiment of this invention.

FIG. 10 is a side elevation.

FIG. 11 is a plan view.

FIG. 12 is an opposite side elevation.

DESCRIPTION OF THE PREFERRED EMBODIMENT

Figure 13:
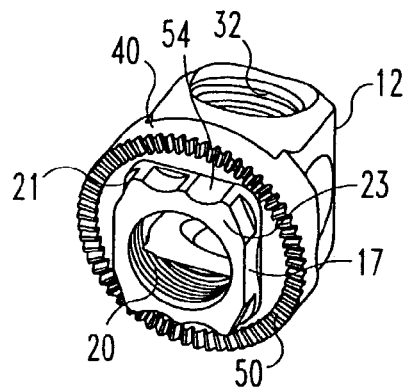
FIG. 13 is a perspective view of a rod connection member with its interface element in place.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

In the illustrated embodiment of the present invention there is provided a connection assembly of reduced size for a spinal implant assembly having interface elements that utilize internal structures to limit rotation of a spinal implant rod in respect to a spinal implant bolt, cause the implant assembly to assume and maintain an initial position approximating its final position, and allow the assembly to be easily secured to maintain the system in an appropriate position. There are shown in FIGS. 1 and 3, views of an assembled connection assembly 10 according to the illustrated embodiment. Corresponding exploded views are shown in FIGS. 2 and 4 illustrating internal details of selected components. The assembly comprises a rod connecting member 12 and a bolt connecting member 22. The rod connecting member 12 has an aperture 14 for receiving a spinal implant rod and a threaded aperture 32 for receiving a securing member such as the set screw for urging the rod within the aperture 14. The bolt connecting member 22 has an aperture 24 for receiving a spinal implant bolt or screw.

The rod connecting member 12 and the bolt connecting member 22 are attached through a rotatable connection. The rotatable connection can be of any suitable design provided the connection is maintained while allowing the rotation of one member relative to the other. Suitable designs include a bolt connecting member 22 having a male protrusion 27 symmetrical about its long or connection axis 13 and a rod connecting member 12 having a female cavity 19 (FIG. 16) for receiving and engaging the male member. In a preferred embodiment, the male and female connections are provided by threaded members such as a screw 30 a threaded female cavity 20 (FIG. 13). Alternatively, the male and female connections could be provided by other suitable male and female connections capable of rotation and simple assembly such as snap-together connections. Connection would occur upon inserting the male protrusion with a flared end portion into the female cavity having a region to accept and retain the flared end portion of the male protrusion.

The rod connecting member 12 has a first interface element 40 fixed against rotation relative to the rod connecting member 12 and the bolt connecting member 22 similarly has a second interface element 41 fixed against rotation relative to the bolt connecting member 22. Interface elements, 40 and 41 are positioned on seats 17 and 26 (FIG. 4), respectively, between the rod and bolt connecting members and are moveable on the seats 17 and 26 between connecting members 12 and 22. External stops 16 and 28 prevent removal of the interface elements 40 and 41. Suitable external stops can include, but are not limited to, a backing face as illustrated by external stop 16 or a surface disruption as can be formed by peening as illustrated by external stop 28.

Figure 15:
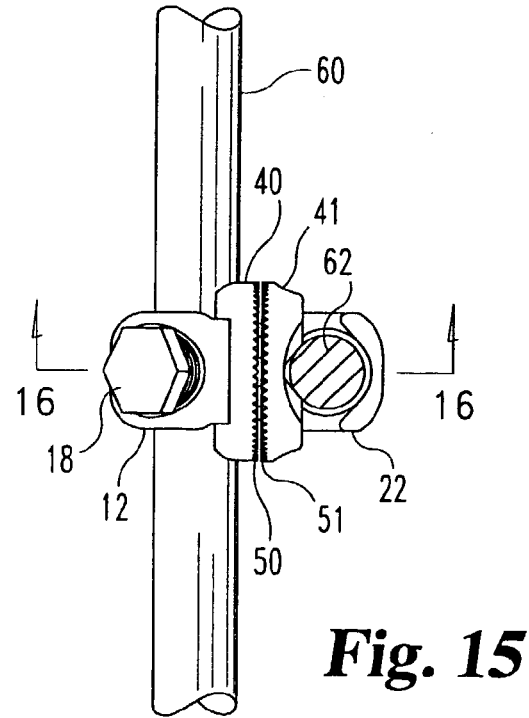
FIG. 15 is a plan view, partially in cross section and nearly secured.
Figure 14:
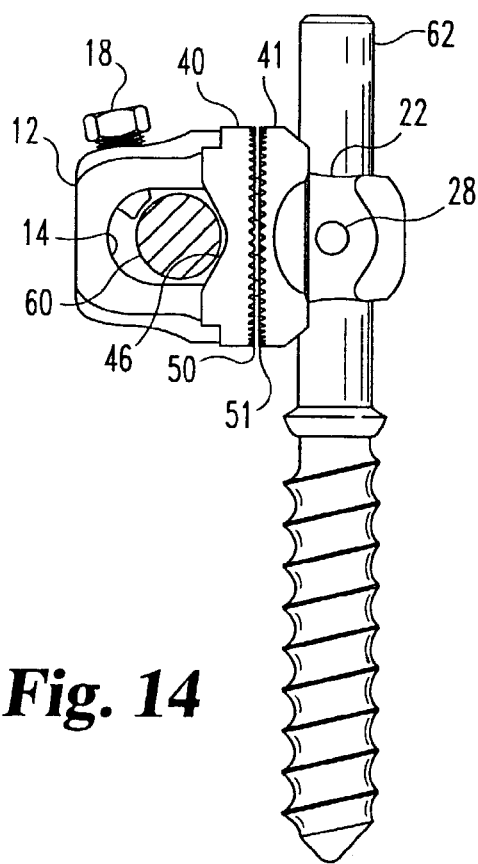
FIG. 14 is a front elevation, partially in cross section, of a spinal implant assembly according to the illustrated embodiment of this invention in a nearly secured mode.

Different views of interface elements 40 and 41 according to this invention are shown in FIGS. 5–12. The interface elements can be of any suitable shape including round as shown. The preferred first interface element 40 has an engagement surface 44 and an engagement groove 46 thereon, running diametrically through the interface element 40. The engagement groove 46 is sized and positioned to engage the spinal implant rod 60 as illustrated in FIG. 14. Similarly the preferred second interface element 41 has an engagement surface 45 similarly having an engagement groove 47 thereon running diametrically through the second interface element 41. Engagement groove 47 is sized and shaped to accept a spinal implant bolt 62 as illustrated in FIG. 15. Preferred interface elements 40 and 41 have generally square or rectangular central openings 48 and 49 which correspond to the size and shape of the cross-section of the respective seats 17 and 26 where interface elements 40 and 41 are positioned. The size and shape of the openings 48 and 49 as well as the size and shape of the cross-sections of seats 17 and 26 can vary as long as both interface elements 40 and 41 are fixed against rotation relative to their respective connecting members 12 and 22, and at least one of the interface elements 40 or 41 is free to move between the connecting elements 12 and 22 on its respective seat 17 or 26.

As shown in FIGS. 5–12, interface elements 40 and 41 have interlocking structures 50 and 51 on the surfaces opposite the engagement surfaces 44 and 45. As shown in FIGS. 1 and 2, the interlocking structures 50 and 51 oppose each other in the completed connection assembly 10 and become engaged when pressed together between the rod connecting member 12 and the bolt connecting member 22. When interlocking structures 50 and 51 are engaged, rotational movement of one interface element and its associated connection member relative to the other interface element and its associated connection member is prevented. Although a variety of interlocking structures can be utilized, such as for example, a plurality of variable angle ridges, circumferential spline teeth as shown in FIGS. 5–12 are preferred. The use of a plurality of variable angle ridges as interlocking structures is described in detail in U.S. Pat. No. 5,643,263, which is hereby incorporated herein by reference in its entirety.

Referring to (FIGS. 3, 4, 12 and 13) novel interface element 41 has an internal stop 52 in the form of a tab located on an inner periphery. The internal stop 52 is sized and positioned to cooperate with two adjacent edges 21 and 23 (FIG. 13) of the seat associated with the rod connecting member to restrict rotation of interface element 40 and rod connecting member 12 in relation to interface element 41 and bolt connecting member 22 to less than about 90 degrees. When assembled, internal stop 52 is positioned between edges 21 and 23 (FIGS. 3, 4 and 13) or any other combination of adjacent edges. Rotation of interface element 41 in either direction causes the internal stop 52 to contact a limiting element, either edge 21 or edge 23, thereby limiting rotation to the arc defined by the two edges 21 and 23. In the present embodiment rotation is limited to less than about 90 degrees. Rotation can be increased by increasing the arc defined by edges 21 and 23 or decreased by decreasing the arc defined by edges 21 and 23. Utilization of the novel internal stop 52 in preferred devices can allow the diameter of interface elements to be reduced from about 16 mm to about 13 mm without reducing the assembly's mechanical strength as compared to prior art devices without an internal stop. Preferred interface elements have a diameter of less than about 16 mm and more preferred interface elements have a diameter between about 15 mm to about 13 mm.

Figure 17:
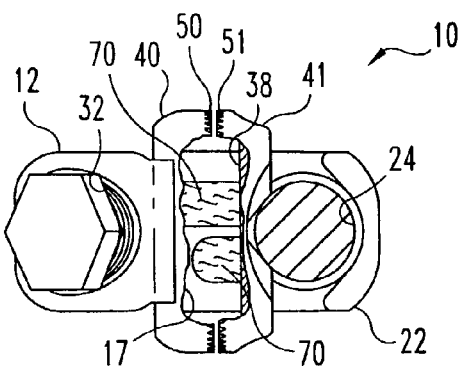
FIG. 17 is a plan view, partially cut away, of a connection assembly showing a compressible member according to the illustrated embodiment, the member in an uncompressed state.
Figure 18:
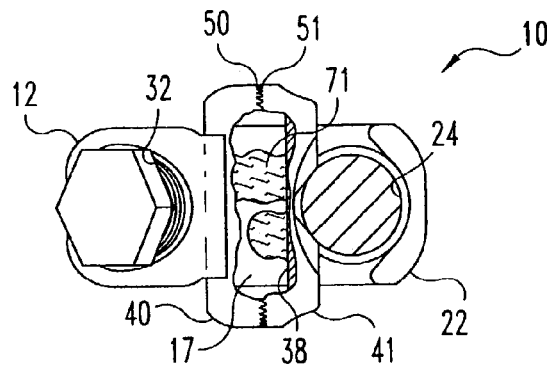
FIG. 18 is a plan view, partially cut away, of a connection assembly showing the compressible member, the member in a compressed state.

In a further embodiment of the present invention, illustrated in FIG. 17, there is provided at least one compressible member 70 fixed to seat 17 (FIGS. 3 and 13) in the region of groove 54 between and in contact with at least the inner face 38 of interface element 41 to maintain a sufficient distance between the interlocking structures 50 and 51 to prevent their engagement while the compressible member 70 is in an uncompressed state. As illustrated in FIG. 18 when set screw 18 is engaged within aperture 32 spinal implant rod 60 is moved toward connecting member 22. Interface elements 40 and 41, positioned between the implant rod 60 and connecting member 22 are forced in the direction of connecting member 22 and toward each other, compressing member 70 against the inner face 38 of interface element 41 and causing interlocking structures 50 and 51 engage. As a result, rotation of interface elements 40 and 41 and their respective connecting elements 12 and 22 is prevented. When the force behind interface element 40 is removed, member 70 resumes its uncompressed state forcing interface elements 40 and 41 apart, causing the interlocking structures to disengage. As a result rotation of the interface elements 40 and 41 and their respective connecting elements 12 and 22 is again possible without any additional effort to separate the interface elements.

Figure 19:
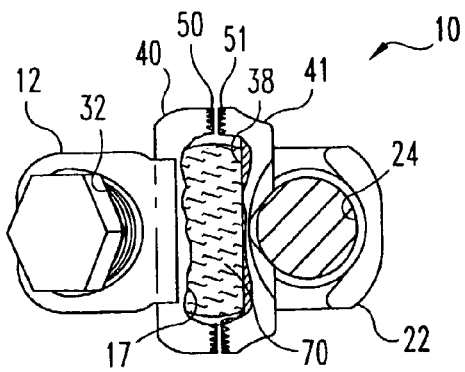
FIG. 19 is a plan view, partially cut away, of a connection assembly showing a compressible member having a generally circular shape according to the illustrated embodiment, the member in an uncompressed state.

Compressible member 70 can be any biocompatible material having the ability to be compressed upon the application of a force and uncompressed upon removal of the force return to its uncompressed state. The biocompatible material can be applied in an uncured form wherein adhesion to the assembly occurs upon curing or in a cured form. Cured forms of member 70 can be maintained in position within assembly 10 either with a biocompatible adhesive or by sizing and shaping member 70 appropriately. An adhesive is unnecessary provided member 70, in its uncompressed form, fits between and contacts the inner faces of interface elements 40 and 41, has a shape that causes it to be secured and prevents engagement of elements 50 and 51. Cured forms of 70 having generally circular shapes have proven particularly useful in this regard (FIG. 19). Preferred compressible members are rubber materials, particularly silicone rubbers and their preferred method of application is to apply the rubber in its uncured form.

Different views of the novel interface elements 40 and 41 according to this invention are shown in FIGS. 5–12. The interface elements can be of any suitable shape including round as shown. Preferred interface elements 40 and 41 have an engagement surfaces 44 and 45 which have engagement grooves 46 and 47, running diametrically through the interface element, the engagement grooves for engaging either a spinal implant rod 60 or a spinal implant bolt 62 in an installed spinal implant assembly illustrated in FIGS. 14 and 15. Preferred interface elements have a generally square or rectangular central opening 48 or 49 that correspond to the cross-sectional shape of the respective seat 17 and 26 to which the interface element is engaged. The size and shape of the openings 48 and 49 can vary as can the size and shape of seats 17 and 26, provided the size and shape of the opening in the first interface element 48 coincides with the size and shape of seat 17 associated with the rod connecting member 12 and provided the size and shape of the opening in the second interface element 41 coincides with the size and shape of seat 26 associated with the bolt connecting member 22.

Figure 16:
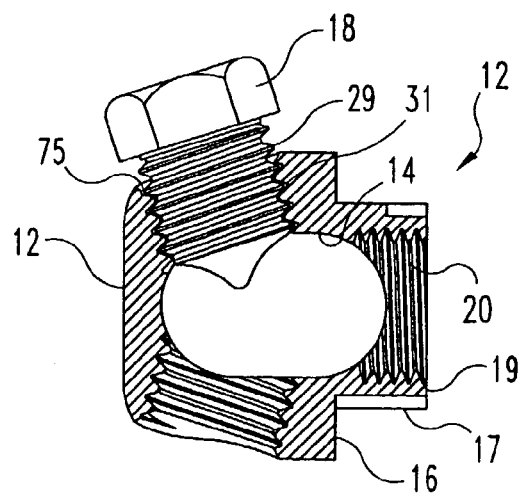
FIG. 16 is a sectional view as at line 16—16 in FIG. 15 and viewed in the direction of the arrows but showing only the rod connecting member and a provisionally secured setscrew according to the illustrated embodiment of this invention.

In a further feature of the illustrated embodiment of the present invention there is provided an assembly for a medical device having a selected component provisionally secured by a material that is disrupted upon installation of the assembly. Medical devices having assemblies with components provisionally secured resist disengagement of the secured components during shipping and related handling. Missing components at the time of installation or implantation are thereby avoided. Illustrated in FIG. 16 is a rod connection member 12 utilized in connection assembly 10 having a set screw 18 provisionally secured by a material 75 surrounding the threads 29 of set screw 18 and the internal threads 31 within aperture 32 (FIG. 13). Suitable materials are biocompatible materials having low to intermediate shear strength that either tear or pull loose from a bonded surface upon the application of minimal force appropriate within a surgical environment. Examples of suitable biocompatible materials are silicone rubbers.

Another feature of this invention is the method for provisionally securing components of a medical device comprising providing at least two components of a medical assembly to be provisionally secured having surfaces suitable for engagement; applying a biocompatible material to at least one of the surfaces; contacting the surfaces to be secured; and maintaining contact of the surfaces until the components have been provisionally secured. An example of biocompatible materials for provisionally securing components of medical devices is silicone rubber. Preferred surfaces particularly suitable to be provisionally secured within components of medical device assemblies include the surface of a male protrusion and the inner surface of an aperture or female cavity suitable for receiving the male protrusion. More preferred surfaces include the threaded surface of a screw and the inner threaded surface of an aperture or female cavity suited for receiving the screw. The time needed for a particular biocompatible material to provisionally secure components of a medical device will vary according to the material selected. Such information is generally available from the material manufacturer or can be determined by one skilled in the art without undue experimentation.

The manner of connection of the connection assembly 10 to a spinal implant rod 60 and a spinal implant bolt 62 is shown in FIGS. 14 and 15. The spinal implant rod 60 and spinal implant bolt 62 are properly positioned within the connecting member 10. Set screw 18, provisionally secured within aperture 32, is threaded into aperture 32 (FIG. 14) where it contacts a side of the spinal implant rod 60, forces rod 60 toward the bolt connecting member 22. The rod 60 contacts the first interface element 40 through its engagement groove 46. As torque is applied to set screw 18, material 75 (FIG. 16) is disrupted allowing set screw 18 to engage aperture 32. As set screw 18 is further threaded into aperture 32, interface element 40 is urged toward interface element 41; member 70 is compressed between interface elements 40 and 41; interlocking structures 50 and 51 are engaged preventing further rotation of rod connecting member 12 and bolt connecting member 22 and interface element 41 engages implant bolt 62 through engagement groove 47. When set screw 18 has been sufficiently engaged, the entire assembly will be locked against movement.

Adjustments can be made by loosening set screw 18 whereby member 70 will become uncompressed, causing interface elements 40 and 41 to move away from each other. As interface elements 40 and 41 are separated, interlocking structures 50 and 51 disengage allowing free rotation of the interface element 40 and rod connecting member 12 with regard to interface element 41 and connecting member 22. After a preferred position has been attained, the assembly can be re-secured by re-tightening set screw 18.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A connection assembly for connecting a spinal implant rod to a spinal implant bolt, the assembly comprising:
    a rod connecting member having an opening for receiving a portion of the rod;
    a first interface element on the rod connecting member;
    a bolt connecting member having an opening for receiving a portion of the bolt;
    a second interface element on the bolt connecting member, the first interface element being fixed against rotation relative to the rod connecting member and the second interface element being fixed against rotation relative to the bolt connecting member, the rod connecting and the bolt connecting members rotatably attached about a connection axis, one member opposing the other;
    interlocking structures on opposing surfaces of the interface elements, such that when the elements are engaged with one another, the interlocking structures prevent rotational movement of the interface elements relative to one another; and
    a compressible member positioned between the interface elements, the compressible member in its uncompressed state preventing the interlocking structures from engaging.

2. The connection assembly of claim 1, wherein at least one of the rod or bolt connecting members has a seat to receive its respective interface element and an external stop, the seat permitting sliding movement of the interface element between the rod and bolt connecting members and the external stop preventing removal of the interface element from its respective member.

3. The connection assembly of claim 2, wherein the rod connecting member and the bolt connecting member are rotatably engaged by corresponding male protrusion and female cavity regions.

4. The connection assembly of claim 3, wherein the interlocking structures are circumferential spline teeth.

5. The connection assembly of claim 4, wherein the compressible member has a generally circular shape that conforms to the outer periphery of a seat.

6. The connection assembly of claim 4 wherein the compressible member is attached to a seat.

7. The connection assembly of claim 4, wherein the compressible member is a polymeric material.

8. The connection assembly of claim 7, wherein the polymeric material is a silicone rubber and is positioned on a seat between the two interface elements.

9. The connection assembly of claim 8, wherein the seat has at least one groove positioned on at least one surface of the seat between the interface elements for receiving the silicone rubber.

10. The connection assembly of claim 4, wherein the male protrusion and female cavity regions are provided by a screw and a threaded opening.

11. The connection assembly of claim 10, wherein an internal stop element is located about the connection axis and fixed within an inner periphery of at least one of the interface elements, the stop cooperating with at least one limiting element to limit rotation of one interface element and its associated member, the limiting element located about the connection axis and associated with an opposing connecting member.

12. The connection assembly of claim 11, wherein the internal stop element comprises a tab positioned to interact with at least two limiting elements, the two limiting elements being edges of the seat associated with the opposing interface element.

13. The connection assembly of claim 12, further comprising:
   at least one securing member extending into the opening of the rod connecting member or the bolt connecting member, contacting and urging the rod or the bolt toward the other, whereby at a first interface element will move along the element's respective seat and be pressed and maintained against a second interface element between the bolt and the rod, preventing rotation of the rod interface element and the rod connecting member relative to the bolt interface element and the bolt connecting member, and securing the rod to the bolt.

14. The connection assembly of claim 13, wherein the securing member is a set screw.

15. The connection assembly of claim 14, wherein at least two members are provisionally secured in their assembled configuration by a biocompatible material, and wherein the biocompatible material is disruptable during installation of the connection assembly.

16. The connection assembly of claim 15, wherein the biocompatible material is a silicone rubber.

17. A connection assembly for connecting a spinal implant rod to a spinal implant bolt, the assembly comprising:
   a rod connecting member having an opening for receiving a portion of the rod, and a first interface element on the rod connecting member;
   a bolt connecting member attached to the rod connecting member, the bolt connecting member having an opening for receiving a portion of the bolt, and a second interface element on the bolt connecting member;
   a compressible member positioned between the first and second interface elements, the compressible member capable of having compressed and uncompressed states;
   the first interface element being fixed against rotation relative to the rod connecting member and the second interface element having a disengaged condition, provided the compressible member is in an uncompressed state, wherein the rod connecting member and bolt connecting member are rotatable within a limited range relative to one another, the limited range defined by an internal stop element positioned within an inner periphery of one of the interface elements; and
   the first interface element and the second interface element having an engaged condition, provided the compressible member is in a compressed state, wherein the rod connecting member and bolt connecting member are fixed against rotation relative to one another.

18. The connection assembly of claim 17, wherein at least one of the rod or bolt connecting members has a seat to receive its respective interface element and an external stop, the seat permitting sliding movement of the interface element between the rod and bolt connecting members and the external stop preventing removal of the interface element from its respective member.

19. The connection member of claim 18, further comprising:
   at least one securing member extending into the opening of the rod connecting member, contacting and urging the rod or the bolt toward the other, whereby at least one of the interface elements will move along its respective seat and will be pressed and maintained together between the bolt and the rod, preventing rotation of the rod interface element and the rod connecting member relative to the bolt interface element and the bolt connecting member, and securing the rod to the bolt.

20. The connection assembly of claim 19, wherein at least two members are provisionally secured in their assembled configurations by a biocompatible material, and wherein the biocompatible material is disruptable during installation of the connection assembly.

21. The connection assembly of claim 20, wherein the securing member is a set screw.

22. The connection assembly of claim 21, wherein the biocompatible material is a silicone rubber.

23. A connection assembly for connecting a spinal implant rod to a spinal implant bolt, the assembly comprising:
   a rod connecting member having an opening for receiving a portion of the rod, and a first interface element on the rod connecting member;
   a bolt connecting member attached to the rod connecting member, the bolt connecting member having an opening for receiving a portion of the bolt, and a second interface element on the bolt connecting member;
   a compressible member positioned between the first and second interface elements, the compressible member capable of having compressed and uncompressed states;
   the first interface element and the second interface element having a disengaged condition, provided the compressible member is in an uncompressed state, wherein the rod connecting member and bolt connecting member are rotatable within a limited range relative to one another, the limited range defined by an internal stop element positioned within an inner periphery of one of the interface elements;
   the first interface element and the second interface element having an engaged condition, provided the compressible member is in a compressed state, wherein the rod connecting member and the bolt connecting member arc fixed against rotation relative to one another.

* * * * *